(12) United States Patent
Orr et al.

(10) Patent No.: US 6,238,351 B1
(45) Date of Patent: May 29, 2001

(54) METHOD FOR COMPENSATING FOR NON-METABOLIC CHANGES IN RESPIRATORY OR BLOOD GAS PROFILE PARAMETERS

(75) Inventors: Joseph A. Orr, Park City, UT (US); Michael B. Jaffe, Cheshire, CT (US); Kai Kück, Hamburg (DE); Dinesh G. Haryadi, Bangalore (IN)

(73) Assignee: NTC Technology Inc., Wilmington, DE (US)

( * ) Notice: Subject to any disclaimer, the term of this patent is extended or adjusted under 35 U.S.C. 154(b) by 0 days.

(21) Appl. No.: 09/150,136

(22) Filed: Sep. 9, 1998

(51) Int. Cl.[7] ..................................................... A61B 5/08
(52) U.S. Cl. ......................... 600/532; 600/529; 600/538; 128/200.24
(58) Field of Search ..................................... 600/500–504, 600/526, 528, 529–543; 128/204.12–204.23, 897–899, 200.24

(56) References Cited

U.S. PATENT DOCUMENTS

| | | |
|---|---|---|
| 4,221,224 | 9/1980 | Clark . |
| 4,463,764 | 8/1984 | Anderson et al. . |
| 5,060,656 | 10/1991 | Howard . |
| 5,069,220 | 12/1991 | Casparie et al. . |
| 5,117,674 | 6/1992 | Howard . |
| 5,178,155 | 1/1993 | Mault . |
| 5,285,794 | 2/1994 | Lynch . |
| 5,299,579 | 4/1994 | Gedeon et al. . |
| 5,402,796 | 4/1995 | Packer et al. . |
| 5,632,281 | * 5/1997 | Rayburn ............................. 600/532 |
| 5,836,300 | * 11/1998 | Mault ................................. 600/532 |
| 5,971,934 | * 10/1999 | Scherer et al. ..................... 600/526 |

FOREIGN PATENT DOCUMENTS

WO 98/12963   4/1998   (WO) .

OTHER PUBLICATIONS

H. Blomquist et al., A Non–Invasive Technique for Measurement of Lung Perfusion, Intensive Care Medicine 1986; 12:172.

R.J. Bosman et al, Non–Invasive Pulimonary Blood Flow Measurement by Means of $CO_2$ Analysis Of Expiratory Gases, Intensive Care Medicine 1991, 17:98–102.

(List continued on next page.)

Primary Examiner—Cary O'Connor
Assistant Examiner—Michael Astorino
(74) Attorney, Agent, or Firm—Trask Britt (57) ABSTRACT

A method of compensating for non-metabolic changes in respiratory or blood gas parameters including generating a compensatory signal based on the magnitude of the non-metabolic change and the amount of time elapsed since the onset of the non-metabolic change. The method of the present invention is useful for compensating for non-metabolic changes in non-invasive carbon dioxide elimination measurements and, particularly, when carbon dioxide elimination is employed to determine cardiac output on a non-invasive, continuous basis.

26 Claims, 4 Drawing Sheets

OTHER PUBLICATIONS

A. Gedeon, Non–Invasive Pulmonary Blood Flow for Optimal Peep, ICOR AB, Ulvsundavagen 178 B, S–161 30 Bromma, Sweden, pp. 49–58.

Capek, J.M., Noninvasive Measurement of Cardiac Output Using Partial $CO_2$ Rebreathing [Dissertation], Rensselaer Polytechnic Institute (1988) 28:351 p. (due to large number of pages, only table of contents and abstract have been copied).

Capek, J.M., et al., Noninvasive Measurement of Cardiac Output Using Partial $CO_2$ Rebreathing, IEEE Trans. Biomed. Eng. (1988) 35(9):653–61.

Davies, Gerald G., et al., Continuous Fick cardiac output compared to thermodilution cardiac output, Critical Care Medicine (1986) 14(10):881–85.

Elliot, C. Gregory, et al., Complications of Pulmonary Artery Catheterization in the Care of Critically Ill Patients, Chest (1979) 76:647–52.

Fick, A., Über die Messung des Blutquantums in den Herzventrikeln, Sitzungsbericht der Physikalisch–Medizinischen Gesellschaft zu Würzburg (1870) 36 (2 pages).

Gama de Abreu, Marcelo, et al., Measurement of Pulmonary Capillary Blood Flow for Trending Mixed Venous Blood Oxygen Saturation and Oxygen Delivery, Crit. Care Med (1998) vol. 26, No. 1 (Suppl), A106, Abstract #238 (1 page).

Gama de Abreu, Marcelo, et al., Is the Partial $CO_2$ Rebreathing Technique a Useful Tool for Trending Pulmonary Capillary Blood Flow During Adjustments of Peep?, Crit. Care Med (1998) vol. 26, No. 1 (Suppl), A106, Abstract #237, (1 page).

Gama de Abreu, et al., Partial carbon dioxide rebreathing: A reliable technique for noninvasive measurement of non-shunted pulmonary capillary blood flow, Crit. Care Med. (1997) 25(4):675–83.

Gedeon, A., et al., Noninvasive Cardiac Output Determined with a New Method Based on Gas Exchange Measurements and Carbon Dioxide Rebreathing: A Study in Animals/Pigs, J. Clin. Monit. (1992) 8(4):267–78.

Gedeon, A., et al., A new method for noninvasive bedside determination of pulmonary blood flow, Med. & Biol. Eng. & Comput. (1980) 18:411–418.

Guyton, A.E., et al., Measurement of cardiac output by the direct Fick method, In: *Cardiac output and its regulation*, W.B. Saunders Company (1973) 21–39.

Kyoku, I., et al. Measurement of cardiac output by Fick method using $CO_2$ analyzer Servo, Kyobu Geka. Japanese Journal of Thoracic Surgery (1988) 41(12):966–70.

Lynch, J., et al., Comparison of a modified Fick method with thermodilution for determining cardiac output in critically ill patients on mechanical ventilation, Intensive Care Med. (1990) 16:248–51.

Mahutte, C. Kees, et al., Relationship of Thermodilution Cardiac Output to Metabolic Measurements and Mixed Venous Oxygen Saturation, Chest (1993) 104(4):1236–42.

Miller, D.M., et al., A Simple Method for the Continuous Noninvasive Estimate of Cardiac Output Using the Maxima Breathing System. A Pilot Study, Anaesth. Intens. Care (1997) 25(1):23–28.

Österlund, B., et al., A new method of using gas exchange measurements for the noninvasive determination of cardiac output: clinical experiences in adults following cardiac surgery, Acta Anaesthesiol Scand (1995) 39:727–32.

Sackner, Marvin A., Measurement of cardiac output by alveolar gas exchange, Handbook of Physiology ~ The Respiratory System IV, Chapter 13, 233–55.

Spalding, H. K., et al., Carbon Dioxide ($CO_2$) Elimination Rate Accurately Predicts Cardiac Output, Anesthesiology (1997) 87(3A) (1 page).

Sprung, Charles L., et al., Ventricular Arrhythmias During Swan–Ganz Catheterization of the Critically Ill, Chest (1981) 79:413–15.

Taskar, V., et al., Dynamics of Carbon Dioxide Elimination Following Ventilator Resetting, Chest (1995) 108:196–202.

Winkler, Tilo, et al., Pulmonary Capillary Blood Flow by Partial $CO_2$ Rebreathing: A Simulation Study Using a Bicompartmental Model of Gas Exchange, Crit Care Med (1998) vol. 26, No. 1 (Suppl), A105, Abstract #234 (1 page).

* cited by examiner

METHOD FOR COMPENSATING FOR NON-METABOLIC CHANGES IN RESPIRATORY OR BLOOD GAS PROFILE PARAMETERS

BACKGROUND OF THE INVENTION

1. Field of the Invention

The present invention relates to methods of compensating for non-metabolic changes in one or more respiratory or blood gas profile parameters of a patient, such as non-metabolic changes caused by changes in ventilation or breathing. Particularly, the present invention relates to methods of compensating for non-metabolic changes in one or more respiratory profile parameters that may be continuously, non-invasively measured. Specifically, the method of the present invention is useful during unstable breathing events for compensating for non-metabolically altered carbon dioxide elimination measurements.

2. Background of Related Art

Many conventional techniques for determining respiratory and cardiac profile parameters may only be performed on an intermittent basis. For example, conventional methods of measuring the cardiac output of a patient, such as indicator dilution and re-breathing techniques, are performed intermittently. Both indicator dilution and re-breathing are useful for determining the cardiac output of a patient.

Indicator dilution, an exemplary invasive, typically intermittent technique for measuring cardiac output, includes introducing a predetermined amount of an indicator into the bloodstream through the heart of a patient and analyzing blood downstream from the point of introduction to obtain a time vs. dilution curve. Thermodilution, in which a room temperature or colder saline solution, which may also be referred to as "cold" saline, is employed as the indicator, is a widely employed type of indicator dilution. Typically, the cold saline is introduced into the right heart bloodstream of a patient through a thermodilution catheter, which includes a thermistor at the end thereof. The thermistor is employed to measure the temperature of the blood after it has passed through the right heart, or downstream from the point at which the cold saline is introduced. A thermodilution curve is then generated from the data, from which the cardiac output of the patient may be derived. Such invasive measurement of cardiac output is, however, somewhat undesirable due to the potential for harming the patient that is typically associated with the introduction and maintenance of a catheter in the pulmonary artery.

Thus, non-invasive techniques for determining cardiac output and pulmonary capillary blood flow have been developed. Cardiac output includes the flow of blood that participates in gas exchange, which is typically referred to as pulmonary capillary blood flow, and the flow of blood that does not participate in the gas exchange, which is typically referred to as intrapulmonary shunt flow, or venous admixture.

The pulmonary capillary blood flow of a patient has been non-invasively determined by employing various respiratory, blood, and blood gas profile parameters in a derivation of the Fick equation, typically either the oxygen ($O_2$) Fick equation or the carbon dioxide ($CO_2$) Fick equation, such as by the use of total or partial re-breathing.

The carbon dioxide Fick equation, which may be employed to non-invasively determine the cardiac output of a patient, follows:

$$Q_t = V_{CO_2}/(C_vCO_2 - C_aCO_2),$$

where $Q_t$ is the cardiac output of the patient, $V_{CO_2}$ is the carbon dioxide elimination of the patient, $C_vCO_2$ is the carbon dioxide content of the venous blood of the patient, and $C_aCO_2$ is the carbon dioxide content of the arterial blood of the patient.

The carbon dioxide elimination of the patient may be non-invasively measured as the difference per breath between the volume of carbon dioxide inhaled during inspiration and the volume of carbon dioxide exhaled during expiration, and is typically calculated as the integral of the carbon dioxide signal times the rate of flow over an entire breath. The volumes of carbon dioxide inhaled and exhaled may each be corrected for any deadspace or intrapulmonary shunt flow.

The partial pressure of end-tidal carbon dioxide ($PetCO_2$ or $etCO_2$) is also measured in re-breathing processes. The partial pressure of end-tidal carbon dioxide during normal breathing, after correcting for any deadspace, is typically assumed to be approximately equal to the partial pressure of carbon dioxide in the alveolar blood ($P_ACO_2$) of the patient or, if there is no intrapulmonary shunt flow or parallel deadspace, the partial pressure of carbon dioxide in the arterial blood ($P_aCO_2$) of the patient.

Conventionally employed Fick methods of determining cardiac output typically include a direct, invasive determination of $C_vCO_2$ by analyzing a sample of the patient's mixed venous blood. A re-breathing process is typically employed either to non-invasively estimate the carbon dioxide content of mixed venous blood (in total re-breathing) or to obviate the need to know the carbon dioxide content of the mixed venous blood (by partial re-breathing). Re-breathing processes typically include the inhalation of a gas mixture which includes carbon dioxide. During re-breathing, the carbon dioxide elimination of the patient decreases. In total re-breathing, the carbon dioxide elimination of the patient decreases to near zero. In partial re-breathing, the carbon dioxide elimination of the patient does not cease. Thus, the decrease of carbon dioxide elimination in partial re-breathing is not as significant as that in total re-breathing.

Figure 1:
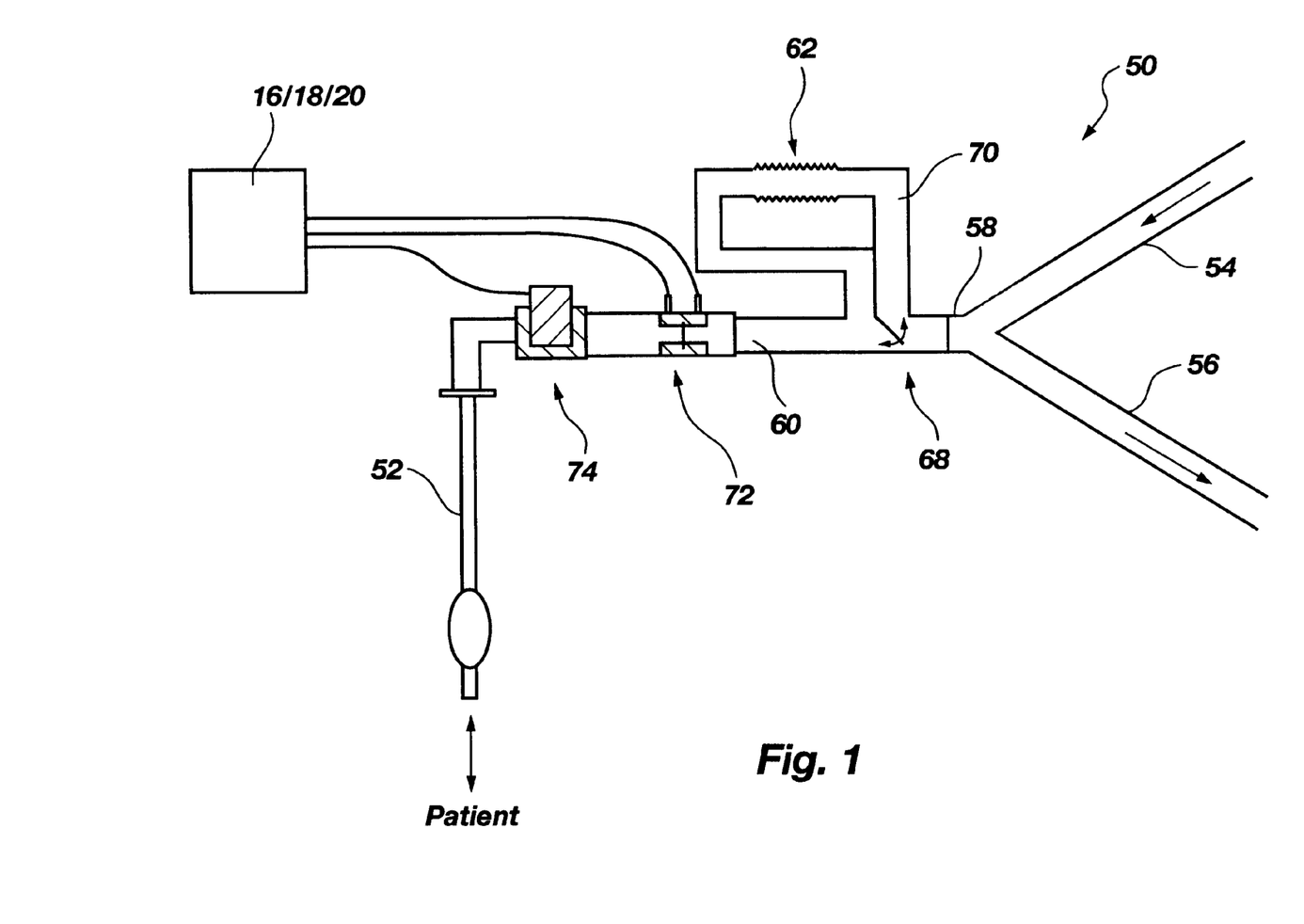
FIG. 1 is a schematic representation of an exemplary re-breathing circuit that may be employed with the methods of the present invention.

Re-breathing is typically conducted with a re-breathing circuit, which causes a patient to inhale a gas mixture that includes carbon dioxide. FIG. 1 schematically illustrates an exemplary re-breathing circuit 50 that includes a tubular airway 52 that communicates air flow to and from the lungs of a patient. Tubular airway 52 may be placed in communication with the trachea of the patient by known intubation processes, or by connection to a breathing mask positioned over the nose and/or mouth of the patient. A flow meter 72, which is typically referred to as a pneumotachometer, and a carbon dioxide sensor 74, which is typically referred to as a capnometer, are disposed between tubular airway 52 and a length of hose 60, and are exposed to any air that flows through re-breathing circuit 50. Both ends of another length of hose, which is referred to as deadspace 70, communicate with hose 60. The two ends of deadspace 70 are separated from one another by a two-way valve 68, which may be positioned to direct the flow of air through deadspace 70. Deadspace 70 may also include an expandable section 62. A Y-piece 58, disposed on hose 60 opposite flow meter 72 and carbon dioxide sensor 74, facilitates the connection of an inspiratory hose 54 and an expiratory hose 56 to re-breathing circuit 50 and the flow communication of the inspiratory hose 54 and expiratory hose 56 with hose 60. During inhalation, gas flows into inspiratory hose 54 from the atmosphere or a ventilator (not shown). During normal breathing, valve 68 is positioned to prevent inhaled and exhaled air from flowing through deadspace 70. During re-breathing, valve 68 is positioned to direct the flow of exhaled and inhaled gases through deadspace 70. During total re-breathing, the partial pressure of end-tidal carbon dioxide ($PetCO_2$) is typically assumed to be equal to the partial pressure of carbon dioxide in the venous blood ($PvCO_2$) of the patient, as well as to the partial pressures of carbon dioxide in the alveolar blood ($PACO_2$) and arterial blood ($PaCO_2$) of the patient. The partial pressure of carbon dioxide in blood may be converted to the content of carbon dioxide in blood by means of a carbon dioxide dissociation curve.

In partial re-breathing, measurements during normal breathing and subsequent re-breathing are substituted into the carbon dioxide Fick equation. This results in a system of two equations and two unknowns (carbon dioxide content in the mixed venous blood and cardiac output), from which pulmonary capillary blood flow can be determined without knowing the carbon dioxide content of the mixed venous blood.

The inability of methods such as indicator dilution and re-breathing to provide continuous measurements of respiratory and cardiac profile parameters is, however, undesirable due to the potential for rapid changes in the measured respiratory or cardiac profile parameter.

Some respiratory and blood gas profile parameters that may only be measured intermittently (e.g., at intervals of about 2 minutes, 5 minutes, 30 minutes, etc.) by noninvasive means have conventionally been assumed to remain relatively steady during stable breathing of a patient and, thus, substantially constant between measurements. An exemplary parameter that remains substantially constant over time periods of several minutes is the difference between the carbon dioxide content of the venous blood ($CvCO_2$) and the carbon dioxide content of the arterial blood ($CaCO_2$), which is typically referred to as the arterial-venous carbon dioxide gradient, or the "AV gradient." The arterial-venous carbon dioxide gradient may be employed in determining cardiac output by means of the carbon dioxide Fick equation.

The arterial-venous carbon dioxide gradient is typically assumed to remain substantially constant over short periods of time (e.g., one minute, five minutes, ten minutes, etc.) as the carbon dioxide stores in the blood and other tissues of the patient remain substantially unchanged. As the foregoing form of the carbon dioxide Fick equation illustrates, the cardiac output measurement also depends upon the carbon dioxide elimination of the patient. When re-breathing is not being conducted, carbon dioxide elimination may typically be accurately determined by measuring the net amount of carbon dioxide exhaled by the patient in each breath and by correcting for any deadspace or intrapulmonary shunt flow. When the ventilation or breathing of the patient changes profoundly, such as during hyperventilation, however, the amount of carbon dioxide exhaled by the patient is non-metabolically altered. Thus, at the beginning of new breathing episodes, the determination of $VCO_2$ by measuring the amount of exhaled carbon dioxide does not accurately reflect the carbon dioxide elimination of the patient. Accordingly, during new breathing episodes, cardiac output could not be accurately, continuously determined on the basis of $VCO_2$ and arterial-venous carbon dioxide gradient.

Alternative differential Fick methods of measuring pulmonary capillary blood flow or cardiac output may be employed in place of the embodiment of the re-breathing method disclosed herein. Such alternative differential Fick methods typically require a brief change of $PetCO_2$ and $VCO_2$ in response to a change in effective ventilation. This brief change can be accomplished by adjusting the respiratory rate, inspiratory and/or expiratory times, or tidal volume. A brief change in effective ventilation may also be effected by adding $CO_2$, either directly or by re-breathing. An exemplary differential Fick method, which is disclosed in Gedeon, A. et al. in 18 *Med. & Biol. Eng. & Comput.* 411–418 (1980), employs a period of increased ventilation followed immediately by a period of decreased ventilation.

Other techniques for determining respiratory and cardiac profile parameters may be performed on a breath-by-breath basis, or continuously. Such methods typically employ the monitoring of at least one blood gas parameter with a catheter (i.e., invasively). Thus, these methods are also somewhat undesirable due to the potential for harm to the patient that is posed by the insertion and use of catheters, as well as the additional costs associated with the use of catheters.

One such technique, disclosed in Davies et al., Continuous Fick cardiac output compared to thermodilution cardiac output, *Crit. Care Med.* (1986) 14:881–885 ("Davies"), includes continuously monitoring the volume of oxygen inspired by the patient ($VO_2$), the oxygen saturation of the patient's venous blood ($SvO_2$), and the oxygen saturation of the patient's arterial blood ($SaO_2$). The determination of cardiac output based on $VO_2$ measurements is, however, somewhat undesirable in that accurate $VO_2$ measurements are typically difficult to obtain, especially when the patient requires an elevated fraction of inspired oxygen ($FiO_2$). Moreover, $SvO_2$ is measured invasively by a pulmonary artery catheter. Thus, the technique disclosed in Davies is not truly non-invasive.

An exemplary non-invasive, continuous method of estimating cardiac output based on the carbon dioxide Fick equation is disclosed in Miller et al., A Simple Method for the Continuous Noninvasive Estimate of Cardiac Output Using the Maxima Breathing System. A Pilot Study, *Anaesth. Intens. Care* 1997; 25:23–28 ("Miller"). The methods of Miller are conducted on the so-called "Maxima" breathing system, which is a valveless, disposable, universal breathing system that selectively substantially eliminates alveolar gas. The methods of Miller, however, may only be performed with the Maxima breathing system. The methods of Miller are further undesirable in that they may only be employed during the stable ventilation of a patient (i.e., while ventilation remains substantially unchanged), when none of the measured parameters have been non-metabolically altered.

Accordingly, a method is needed that generates a signal that compensates for non-metabolic changes in one or more respiratory or blood gas profile parameters in order to facilitate the accurate determination of other respiratory, blood gas, or cardiac profile parameters that are not directly, continuously measurable.

SUMMARY OF THE INVENTION

The compensatory methods of the present invention address the foregoing needs.

The method of the present invention compensates for non-metabolic changes in one or more respiratory or blood gas profile parameters of a patient. Accordingly, in a preferred embodiment of the method, when a change in the ventilation or respiration of a patient has been detected (i.e., the ventilation of the patient becomes temporarily unstable), a compensatory signal, or correction factor, is generated. The compensatory signal modifies at least one of the parameters in order to facilitate the substantially accurate estimation of another respiratory, blood gas, or cardiac profile parameter while the instability or non-metabolic change persists. For example, it takes up to about 30 minutes for a non-invasively determined $V_{CO_2}$ measurement to return to "normal" following a profound change in ventilation, which is also referred to as a "new" breathing episode, such as an adjustment in mechanical ventilation.

Since non-metabolic changes in respiratory and blood gas profile parameters gradually return to normal, the magnitude of the compensatory signal diminishes at an approximately proportionate rate to the decrease in the magnitude of the difference between the measured, non-metabolically altered parameter and a "normal" or average value for that parameter during stable ventilation or breathing. Thus, the amount of time that has elapsed since the onset of the new breathing episode that caused the non-metabolic change and the magnitude of the difference between the normal value of each of the non-metabolically altered respiratory profile parameters and the measured value of these respiratory profile parameters are considered in determining the value of the compensatory signal at any given moment.

In the preferred embodiment, the method of the present invention may be employed to compensate for non-metabolic changes in the measured carbon dioxide elimination of a patient in order to facilitate accurate estimation of the cardiac output of the patient during or following profound changes in ventilation or breathing. The preferred embodiment includes determining or estimating the arterial-venous ("AV") carbon dioxide gradient of the patient under normal ventilation conditions, detecting a change in the ventilation of the patient, measuring the amount of carbon dioxide eliminated by the patient, generating a compensatory signal, and calculating cardiac output or pulmonary capillary blood flow by employing the measured carbon dioxide elimination, the arterial-venous carbon dioxide gradient, and the compensatory signal.

Other advantages of the present invention will become apparent to those in the art through a consideration of the ensuing description, the accompanying drawings and the appended claims.

DETAILED DESCRIPTION OF THE PREFERRED EMBODIMENT

The present invention includes a method of compensating for non-metabolic changes in one or more respiratory or blood gas profile parameters of a patient. A preferred embodiment of the method according to the present invention, which is useful for accurately estimating cardiac output, which is also referred to as an "estimated parameter", during new breathing episodes, includes compensating for non-metabolic changes in the measured carbon dioxide elimination of the patient during such unstable breathing to facilitate the accurate estimation of the cardiac output of the patient on a breath-by-breath basis.

Cardiac output may be non-invasively determined in accordance with a form of the carbon dioxide Fick equation:

$$Q = V_{CO_2}/(C_vCO_2 - C_aCO_2),$$

where the denominator, ($C_vCO_2 - C_aCO_2$), represents the arterial-venous carbon dioxide gradient of the patient. Since the arterial-venous carbon dioxide gradient remains substantially constant while carbon dioxide stores in the blood or other tissues of a patient remain substantially unchanged, cardiac output may be measured continuously, on a breath-by-breath basis, by measuring the patient's $V_{CO_2}$ while the carbon dioxide stores remain substantially unchanged. Typically, $V_{CO_2}$ may be accurately, non-invasively measured by determining the volume of carbon dioxide exhaled by the patient. When the ventilation or breathing of the patient changes abruptly, which is also referred to as a new breathing episode, however, the amount of carbon dioxide eliminated by the patient is altered until after a new equilibrium point between carbon dioxide elimination and carbon dioxide excretion has been established and the breathing instability subsides. Initially, the change in the $V_{CO_2}$ measurement is non-metabolic. After the carbon dioxide stores of the blood or other tissues of the patient have increased to their pre-new breathing episode levels, however, the $V_{CO_2}$ returns to its metabolic value. Thus, during new breathing episodes, non-invasive $V_{CO_2}$ measurements are typically altered.

Preferably, the arterial-venous carbon dioxide gradient of the patient is determined while the ventilation or breathing of the patient is stable by employing intermittent means for determining cardiac output. Examples of intermittent means for determining cardiac output that may be employed in the inventive method include, without limitation, known invasive techniques (e.g., indicator dilution techniques, such as thermodilution) or non-invasive techniques (e.g., partial or total re-breathing). A $V_{CO_2}$ measurement, which may be obtained by known means, such as those disclosed below in reference to FIG. 3, may then be divided by the cardiac output measurement to determine the arterial-venous carbon dioxide gradient of the patient.

Figure 2:
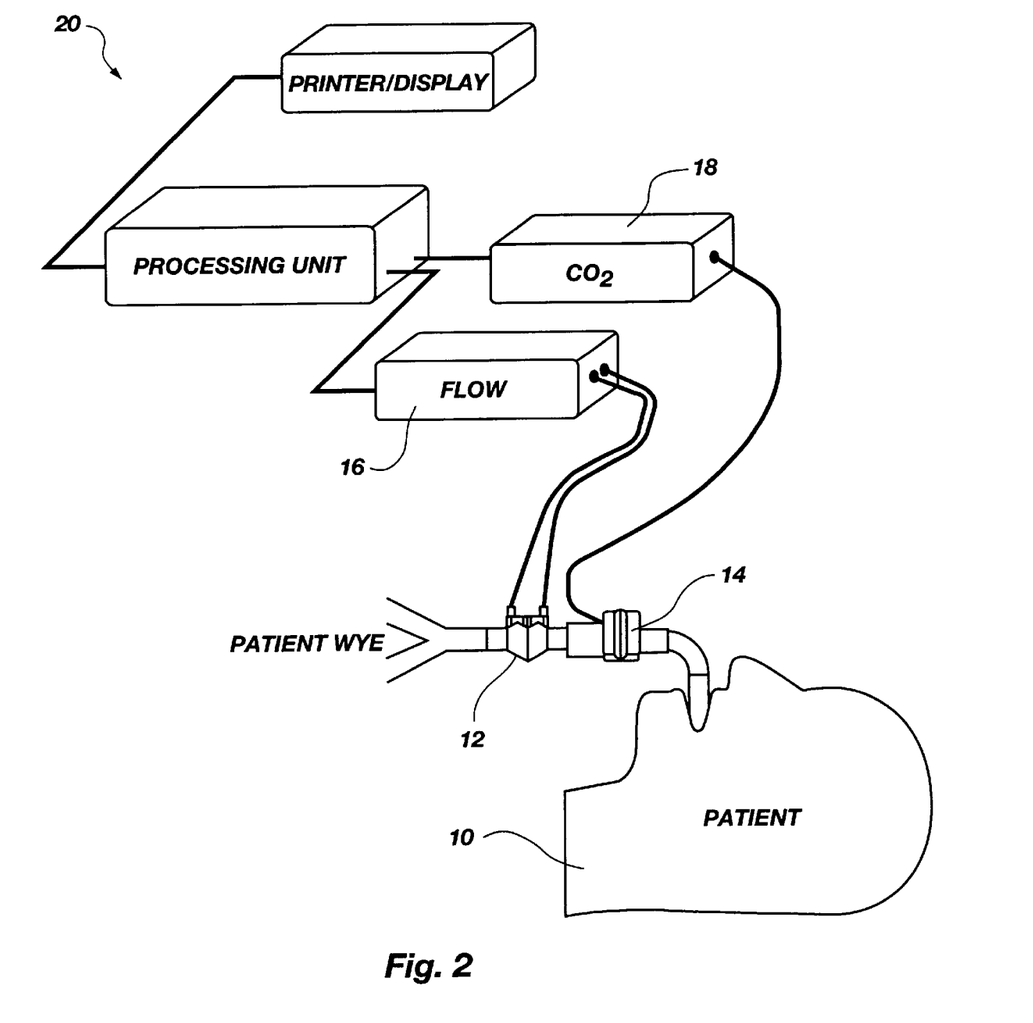
FIG. 2 is a schematic representation which illustrates the various componentry that may be utilized to measure respiratory profile parameters that are employed in the methods of the present invention.
Figure 3:
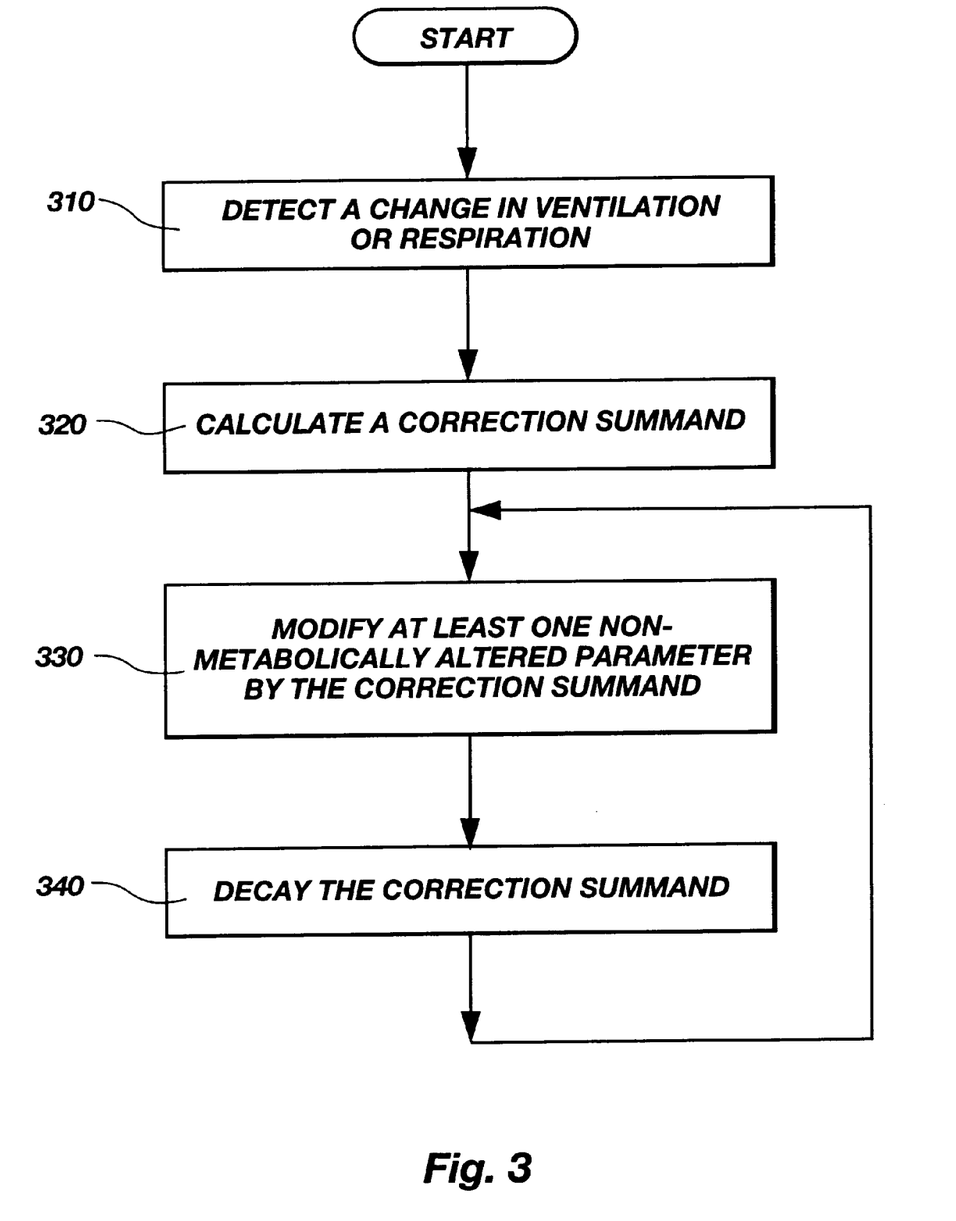
FIG. 3 is a flow chart that schematically illustrates the methods of the present invention.

Referring now to FIG. 3, at reference 310, a change in the ventilation of a patient may be detected by monitoring either the carbon dioxide elimination of the patient or the end tidal partial pressure of $CO_2$ exhaled by the patient or by directly monitoring or measuring the ventilation of the patient. With reference to FIG. 2, carbon dioxide elimination or end tidal $CO_2$ is preferably determined non-invasively by measuring the flow rates and $CO_2$ fraction of gas mixtures that are inhaled and exhaled by a patient 10 over the course of the patient's breathing. A flow sensor 12 of a known type, such as the differential-pressure type respiratory flow sensors manufactured by Novametrix Medical Systems Inc. of Wallingford, Conn. (e.g., the Pediatric Flow/Adult Flow Sensor (Catalog No. 6717) or the Neonatal Flow Sensor (Catalog No. 6718)), as well as respiratory flow sensors based on other operating principles and manufactured and marketed by Novametrix or others, which may be operatively attached to a ventilation apparatus (not shown), may be employed to measure the flow rates of the breathing of patient 10. A $CO_2$ sensor 14, such as the CAPNOSTAT®

$CO_2$ sensor and a complementary airway adapter (e.g., the Pediatric/Adult Single Patient Use Airway Adapter (Catalog No. 6063) or the Neonatal/Pediatric Reusable Airway Adapter (Catalog No. 7053)), which are manufactured by Novametrix, as well as main stream or side stream $CO_2$ sensors manufactured or marketed by Novametrix or others, may be employed to measure the $CO_2$ fractions of gas mixtures that are inhaled and exhaled by patient 10. Flow sensor 12 and $CO_2$ sensor 14 are connected to a flow monitor 16 and a $CO_2$ monitor 18, respectively, each of which may be operatively associated with a computer 20 so that data from the flow and $CO_2$ monitors 16 and 18 representative of the signals from each of flow sensor 12 and $CO_2$ sensor 14 may be detected by computer 20 and processed according to programming (e.g., by software) thereof. Preferably, raw flow and $CO_2$ signals from the flow monitor and $CO_2$ sensor are filtered to remove any significant artifacts. As several respiratory flow and $CO_2$ pressure measurements are made, the respiratory flow and $CO_2$ pressure data may be stored by computer 20. Thus, cardiac output may be calculated, in accordance with the foregoing equation or by any other suitable equation known in the art, by computer 20.

Each breath, or breathing cycle, of patient 10 may be delineated as known in the art, by continuously monitoring the flow rate of the breathing of patient 10.

A substantial change (e.g., 5, 10, or 20%) in $V_{CO_2}$ or $PetCO_2$, relative to at least one $V_{CO_2}$ or $PetCO_2$ measurement or an average of several $V_{CO_2}$ or $PetCO_2$ measurements taken before the unstable breathing episode, may be considered as a change in ventilation or breathing. Alternatively, a change in breathing or ventilation may be indicated by a substantial change in the respiratory rate of the patient, or by a substantial change in a tidal volume of the patient's respiration.

Referring again to FIG. 3, at reference 320, once a change in ventilation or breathing has been detected, a compensatory signal, or correction factor, is generated in order to compensate for the non-metabolic change and, thus, provide for a more accurate cardiac output estimate. The compensatory signal may be generated based on a variety of factors, including, without limitation, the amount of time that has elapsed since the onset of a new breathing episode, the type of change in ventilation or breathing (e.g., hyperventilation), the condition of the patient's lungs, and the magnitude of change in the measured carbon dioxide elimination relative to the stable, or "normal" carbon dioxide elimination, as measured or estimated prior to the new breathing episode. Since a non-metabolic change in the carbon dioxide elimination measurement that is caused by a new breathing episode, such as unstable ventilation or breathing or a profound change in ventilation or breathing, gradually diminishes over time, the compensatory signal is preferably adjusted over time in a similar manner. Adjusting the compensatory signal in this manner facilitates the continued, substantially accurate estimation of cardiac output while the new breathing episode persists and following the change in ventilation or breathing.

An exemplary compensatory signal may be generated by employing a time constant that may be based upon a model of the duration of a particular cause or type of change in ventilation or breathing (e.g., hyperventilation). Preferably, the amount of time that has elapsed since the onset of the new breathing episode and the magnitude of the non-metabolic change in one or more respiration (e.g., carbon dioxide elimination or end tidal volume of carbon dioxide) or blood gas profile parameters are considered in generating the compensatory signal.

Figure 4:
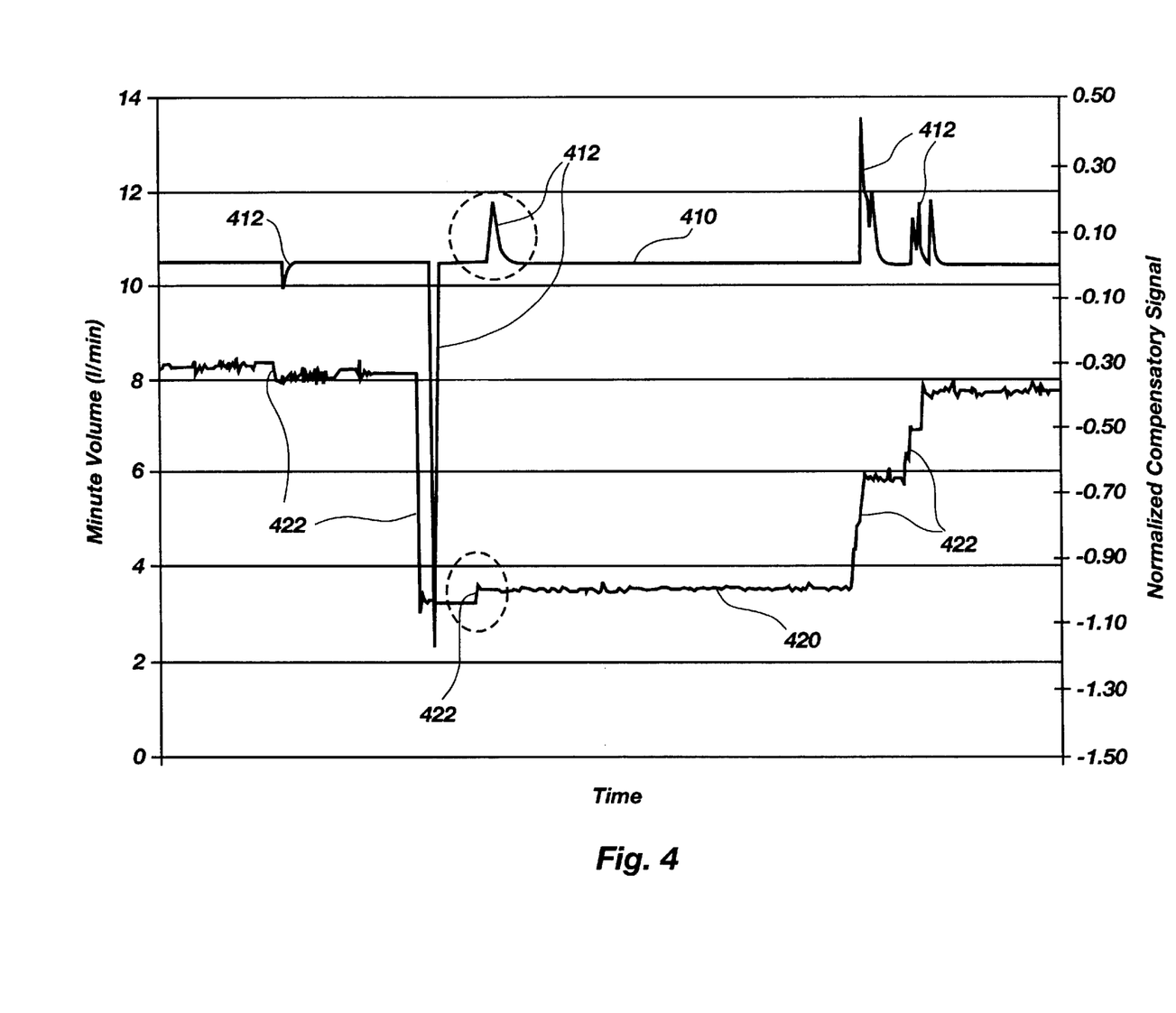
FIG. 4 is a line graph showing a change in respiration of a patient and a normalized compensatory signal generated to offset the change in respiration.

FIG. 4 is a line graph that illustrates a normalized compensatory signal 410 that may be generated in response to changes in the ventilation of the patient. The ventilation of the patient is represented by a respiration graph line 420. Changes in ventilation 422 of respiration graph line 420 are compensated for by changes 412 of equivalent magnitude in normalized compensatory signal 410.

As an example of how a compensatory signal may be generated, if a sudden or step change in the monitored signal is observed, the amount of the step change is assumed to be caused by the non-metabolic change in ventilation. At reference 340 of FIG. 3, the compensating signal may be an exponentially decreasing signal with an initial magnitude equal to the size of the step change and decreasing by a fixed percentage with each subsequent breath. For example, if the step change was an increase in $V_{CO_2}$ from about 200 to about 300 ml per minute, a compensating signal may have an initial value of 100 and may be reduced by 3% for each subsequent breath (i.e., 100, 97, 94, 91, etc.). This compensatory signal would be subtracted from the measured $V_{CO_2}$ value for each breath until the compensatory signal reaches zero, thus maintaining a $V_{CO_2}$ signal that reflects the metabolic level of about 200 ml of $CO_2$ produced per minute, preferably until the non-metabolic change corrects itself.

One or more of the respiratory or blood gas profile parameters (e.g., $V_{CO_2}$ or AV gradient) are modified by the compensatory signal, at reference 330 of FIG. 3, to facilitate the accurate estimation of cardiac output or pulmonary capillary blood flow on a breath-by-breath basis. Either non-metabolically altered or unaltered parameters may be modified.

Cardiac output or pulmonary capillary blood flow may then be determined from the $V_{CO_2}$ and arterial-venous gradient measurements, as modified, by the carbon dioxide Fick equation.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. A method of compensating for non-metabolic changes in a respiratory profile parameter of a patient, comprising:
   detecting an onset of a non-metabolic change;
   generating a compensatory signal in response to the non-metabolic change; and
   employing said compensatory signal in calculating the respiratory profile parameter.

2. The method of claim 1, wherein said detecting said onset comprises detecting a substantial change in a partial pressure of end-tidal carbon dioxide of the patient.

3. The method of claim 1, wherein said detecting said onset comprises detecting a substantial change in a respiratory rate of the patient.

4. The method of claim 1, wherein said detecting said onset comprises detecting a substantial change in a tidal volume of the patient.

5. The method of claim 1, wherein said detecting said onset comprises detecting a substantial change in carbon dioxide elimination of the patient.

6. The method of claim 1, wherein said generating said compensatory signal comprises considering an amount of time elapsed since said onset.

7. The method of claim 1, wherein said generating said compensatory signal comprises considering a magnitude of said non-metabolic change.

8. The method of claim 1, further comprising estimating a stable respiratory profile parameter of the patient.

9. The method of claim 8, wherein said employing said compensatory signal comprises calculating a difference between said stable respiratory profile parameter and said compensatory signal.

10. A method of compensating for non-metabolic changes in carbon dioxide elimination of a patient, comprising:

detecting a change in ventilation of the patient;

non-invasively determining the carbon dioxide elimination of the patient;

estimating an arterial-venous gradient of the patient;

generating a compensatory signal in response to said change in ventilation and a magnitude of a non-metabolic change in carbon dioxide elimination; and calculating a cardiac output of the patient by modifying at least one of the carbon dioxide elimination and said arterial-venous gradient and dividing the carbon dioxide elimination by said arterial-venous gradient.

11. The method of claim 10, wherein said estimating said arterial-venous gradient comprises determining said arterial-venous gradient prior to said change in ventilation.

12. The method of claim 10, wherein said estimating said arterial-venous gradient comprises employing a model based at least in part on a type of said change in ventilation.

13. The method of claim 10, wherein said estimating said arterial-venous gradient comprises employing a model based at least on a condition of said patient.

14. The method of claim 10, further comprising continuously monitoring at least one blood gas parameter of the patient.

15. The method of claim 14, wherein said at least one blood gas parameter is selected from the group comprising carbon dioxide content of arterial blood, carbon dioxide content of venous blood, oxygen content of arterial blood, oxygen content of venous blood, oxygen content of end capillary blood, partial pressure of oxygen in venous blood, partial pressure of oxygen in arterial blood, oxygen saturation of venous blood, and oxygen saturation of arterial blood.

16. The method of claim 10, wherein said detecting said change in ventilation comprises detecting a substantial change in a partial pressure of end-tidal carbon dioxide.

17. The method of claim 10, wherein said detecting said change in ventilation comprises detecting a substantial change in said carbon dioxide elimination of the patient.

18. The method of claim 10, wherein said detecting comprises detecting a substantial change in a respiratory rate of the patient.

19. The method of claim 10, wherein said detecting comprises detecting a substantial change in a tidal volume of the patient.

20. The method of claim 10, wherein said estimating said arterial-venous gradient is effected by a cardiac output determination comprising Fick cardiac output re-breathing.

21. The method of claim 20, wherein said re-breathing comprises total re-breathing or partial re-breathing.

22. The method of claim 10, wherein said estimating said arterial-venous gradient is effected by a differential Fick technique comprising adjusting a respiratory rate, adjusting an inspiratory time, adjusting an expiratory time, adjusting a tidal volume, or adding carbon dioxide to respiration of the patient.

23. The method of claim 10, wherein said generating said compensatory signal comprises considering an amount of time elapsed since an onset of said change in ventilation.

24. The method of claim 23, wherein said generating said compensatory signal comprises employing a model based on said magnitude and said amount of time.

25. The method of claim 10, wherein, in said generating said compensatory signal, said magnitude is based on a change in a partial pressure of end tidal carbon dioxide of the patient.

26. The method of claim 10, wherein, in said generating said compensatory signal, said magnitude is based on a change in carbon dioxide elimination of the patient.

* * * * *

UNITED STATES PATENT AND TRADEMARK OFFICE
CERTIFICATE OF CORRECTION

| | |
|---|---|
| PATENT NO. | : 6,238,351 B1 |
| APPLICATION NO. | : 09/150136 |
| DATED | : May 29, 2001 |
| INVENTOR(S) | : Joseph A. Orr et al. |

Page 1 of 1

It is certified that error appears in the above-identified patent and that said Letters Patent is hereby corrected as shown below:

On the title page:
In item (54) Title,   LINE 1,   after "METHOD" change "FOR" to --OF--

In the Specification:
COLUMN 1,   LINE 1,   after "METHOD" change "FOR" to --OF--

Signed and Sealed this

Tenth Day of July, 2007

JON W. DUDAS
*Director of the United States Patent and Trademark Office*